(12) United States Patent
Abnett

(10) Patent No.: US 6,691,560 B2
(45) Date of Patent: Feb. 17, 2004

(54) FREE ROTOR VISCOMETER

(76) Inventor: Albert C. Abnett, 14250 T.H.135, Nevada, OH (US) 44849

( * ) Notice: Subject to any disclaimer, the term of this patent is extended or adjusted under 35 U.S.C. 154(b) by 0 days.

(21) Appl. No.: 10/001,576

(22) Filed: Nov. 2, 2001

(65) Prior Publication Data

US 2003/0084708 A1 May 8, 2003

(51) Int. Cl.⁷ ................................................. G01N 11/16
(52) U.S. Cl. .................... 73/54.28; 73/54.31; 73/54.35; 73/54.38
(58) Field of Search ........................... 73/54.01, 54.23, 73/54.28, 54.31, 54.35, 54.38

(56) References Cited

U.S. PATENT DOCUMENTS

| | | | |
|---|---|---|---|
| 2,572,693 A | | 10/1951 | Boyle |
| 2,574,973 A | | 11/1951 | Hughes |
| 3,122,914 A | * | 3/1964 | Stabe et al. ................ 73/54.38 |
| 4,637,250 A | | 1/1987 | Irvine, Jr. et al. |
| 4,643,021 A | * | 2/1987 | Mattout ..................... 73/54.28 |
| 4,750,351 A | | 6/1988 | Ball |
| 5,448,908 A | | 9/1995 | El Bounia et al. |
| 5,597,949 A | | 1/1997 | Kalotay |
| 5,798,454 A | | 8/1998 | Nakazeki et al. .......... 73/54.28 |

FOREIGN PATENT DOCUMENTS

| | | | | |
|---|---|---|---|---|
| DE | 3714708 | * | 2/1988 | ............... 73/54.28 |
| GB | 1244408 | * | 9/1971 | ............... 73/54.28 |
| SU | 482655 | * | 8/1975 | ............... 73/54.33 |
| SU | 1672303 | * | 8/1991 | ............... 73/54.28 |
| SU | 1755117 | * | 8/1992 | ............... 73/54.28 |
| WO | 86/00408 | * | 1/1986 | ............... 73/54.35 |

* cited by examiner

*Primary Examiner*—Daniel S. Larkin
(74) *Attorney, Agent, or Firm*—David G. Herold

(57) ABSTRACT

A rotary viscometer is described where there is no mechanical linkage between a rotor that is rotated in a test fluid to measure viscosity and the rotor drive source. A rotor is disposed in a test fluid within a test chamber. The rotor is mounted on low friction bearings. Electromagnets disposed around the test chamber impose a constant torque on the rotor. Rotor rotation rate corresponding to fluid viscosity is measured. The viscometer may have a sealed test chamber for measuring viscosity of hazardous or corrosive test fluids without exposing the operator to the fluid.

21 Claims, 9 Drawing Sheets

| Rotor Position (Degrees) | Energized Electromagnet | Pulled Rotor Pole | Magnetic Polarity |
|---|---|---|---|
| 0-30 | G | B | N |
| 30-60 | H | C | N |
| 60-90 | F | D | N |
| 90-120 | G | A | S |
| 120-150 | H | B | S |
| 150-180 | F | C | S |
| 180-210 | G | D | S |
| 210-240 | H | A | N |
| 240-270 | F | B | N |
| 270-300 | G | C | N |
| 300-330 | H | D | N |
| 330-360 | F | A | S |
| 360-390 | G | B | S |
| 390-420 | H | C | S |
| 420-450 | F | D | S |
| 450-480 | G | A | N |
| 480-510 | H | B | N |
| 510-540 | F | C | N |
| 540-570 | G | D | N |
| 570-600 | H | A | S |
| 600-630 | F | B | S |
| 630-660 | G | C | S |
| 660-690 | H | D | S |
| 690-720 | F | A | N |

FIG. 3

FREE ROTOR VISCOMETER

BACKGROUND

1. Field of Invention

This invention relates to viscometry and specifically to free rotor viscometry, where there is no mechanical linkage between a rotor that is rotated in a test fluid to measure viscosity and the rotor drive source.

2. Description of Prior Art

Viscosity measurements are useful in many endeavors involving fluid handling and processing. In response, many different methods and devices have been devised to measure viscosity. Many applications need to accurately measure viscosity with a small amount of test fluid. In the area of hazardous or corrosive fluids, there is a need to measure viscosity without exposing the operator to the fluid under test. The available viscosity measurement technologies do not adequately address these needs.

A number of available viscometers consist of a motor directly coupled to a rotor, which rotates in the test fluid. Motor torque or rotation rate is measured from which fluid viscosity may be determined. Brookfield Engineering has a number of popular viscometers that operate this way. One of the drawbacks with this approach is the difficulty in sealing the motor shaft for applications requiring viscosity to be measured at nonstandard pressures or when the viscosity of hazardous or corrosive material is being measured. If the motor drive shaft is sealed, friction between the drive shaft and the seal decreases the accuracy of the viscosity measurement. U.S. Pat. Nos. 2,574,973 and 2,572,693 describe variations of this type of viscometer.

U.S. Pat. No. 5,448,908 describes an approach to measuring the viscosity of fluids with very low viscosities. However, the problem of accurately measuring viscosity in a sealed container remains. In addition, this approach would require a large amount of the test fluid and it would be difficult to assure that the entire volume of test fluid was at the desired temperature during the viscosity measurement.

U.S. Pat. No. 5,798,454 discloses a magnetically suspended rotor disposed in the test fluid and rotated magnetically. The position of the suspended rotor is perturbed laterally and viscosity is calculated from the time required for the rotor to return to its unperturbed position. This invention is designed to be an integral part of a blood pump and measures the viscosity of blood flow. This invention does not measure viscosity of a small sample of test fluid nor is it adaptable to a disposable test chamber.

OBJECTS AND ADVANTAGES

It is therefore an object of the present invention to provide an accurate viscosity measure.

It is a further object of the present invention to measure fluid viscosity at two or more temperatures.

It is a further object of the present invention to operate in any orientation.

It is a further object of the present invention to measure the viscosity of a test fluid with a small sample of the test fluid.

It is a further object of the present invention to measure the viscosity of a test fluid of low viscosity.

It is a further object of the present invention to make continuous measurements of viscosity.

It is a further object of the present invention to make viscosity measurements on a test fluid sealed within a disposable test chamber.

SUMMARY

According to the present invention an apparatus and method for accurate measurement of the viscosity of small fluid samples have been developed. The invention is easily adapted to providing a disposable sealed test chamber to contain hazardous or corrosive test fluids during viscosity measurement.

In the preferred embodiment of the invention, a viscosity tester for fluid comprises a centrally disposed test chamber for containing the fluid, said test chamber having a cylindrical side wall, a circular bottom wall and a circular top wall, the top and bottom walls have perimeters at side wall junctions. A generally cylindrical rotor is disposed in the fluid, the rotor is rotataby supported by bearings on an axis of rotation. The rotor has a plurality of magnetic poles disposed about the axis. A plurality of electromagnets are mounted in positions spaced around the chamber side wall. A plurality of proximity sensors are embedded in the chamber bottom wall, a unique proximity sensor being associated with each of the electromagnets, each proximity sensor producing a sensor signal when a rotor pole is radially aligned with the associated electromagnet. A control system is interconnected with a power supply, the electromagnets and the proximity sensors for selectively energizing the electromagnets sequentially in response to the sensor signals for imposing magnetic forces on the rotor, producing a rotor torque and rotating the rotor within the fluid at a rotation rate. A means for producing an output signal corresponding to the viscosity of the fluid based on rotor torque and rotation rate produces a signal corresponding to fluid viscosity.

In another embodiment of the invention, a viscosity tester for fluid comprises a removable test chamber and a test fixture. The removable test chamber comprises a tube with a closed-end bottom and a circular opening at a top end, the circular opening is sealed by a cap disposed over the opening and engaging the tube, the cap has an inside surface. The removable test chamber contains the fluid and a rotor disposed in the fluid. The rotor is rotatably supported on an axis of rotation on bearings mounted on the inside surface of the cap and on the closed-end bottom of the tube. The rotor further comprises a plurality of magnetic poles disposed about the axis and a position sense magnet. The removable test chamber is supported vertically in the test fixture. The test fixture comprises a plurality of electromagnets, a plurality of proximity sensors, a power supply, a control system, and means for producing an output signal corresponding to fluid viscosity. The plurality of electromagnets are mounted in positions spaced around and proximate to said removable test chamber. The plurality of proximity sensors are mounted in positions spaced around and proximate to said removable test chamber, a unique proximity sensor being associated with each of the electromagnets, each proximity sensor sensitive to the proximity of the rotor position sense magnet and producing a sensor signal when a rotor pole is radially aligned with the associated electromagnet. The control system is interconnected with the power supply, the electromagnets, and the proximity sensors for selectively energizing said electromagnets sequentially, in response to the sensor signals, for imposing magnetic forces on said rotor, producing a rotor torque, and rotating the rotor within the fluid at a rotation rate. The means for producing an output signal corresponding to fluid viscosity based on rotor torque and rotation rate produces a signal corresponding to fluid viscosity.

In accordance with a more general aspect of the invention, an apparatus for measuring the viscosity of a fluid comprises a test chamber for containing the fluid and a rotor disposed in the fluid. The rotor is rotatably supported by a low-friction support means on an axis of rotation. The rotor has a plurality of magnetic poles disposed about the axis. A magnet means produces a magnetic field and imposes a magnetic force on the magnetic poles, producing a rotor torque causing the rotor to rotate in the fluid at a rotation rate. A control means controls one of rotor torque and rotation rate. A sensing means senses one of rotation rate and rotor torque and produces a signal corresponding to the viscosity of the fluid.

BRIEF DESCRIPTION OF THE DRAWINGS

The foregoing features and other aspects of the invention will be described further in detail by reference to the accompanying drawings, in which:

FIG. 3 is a table showing the electromagnet commutation pattern.

DESCRIPTION

Figure 1:
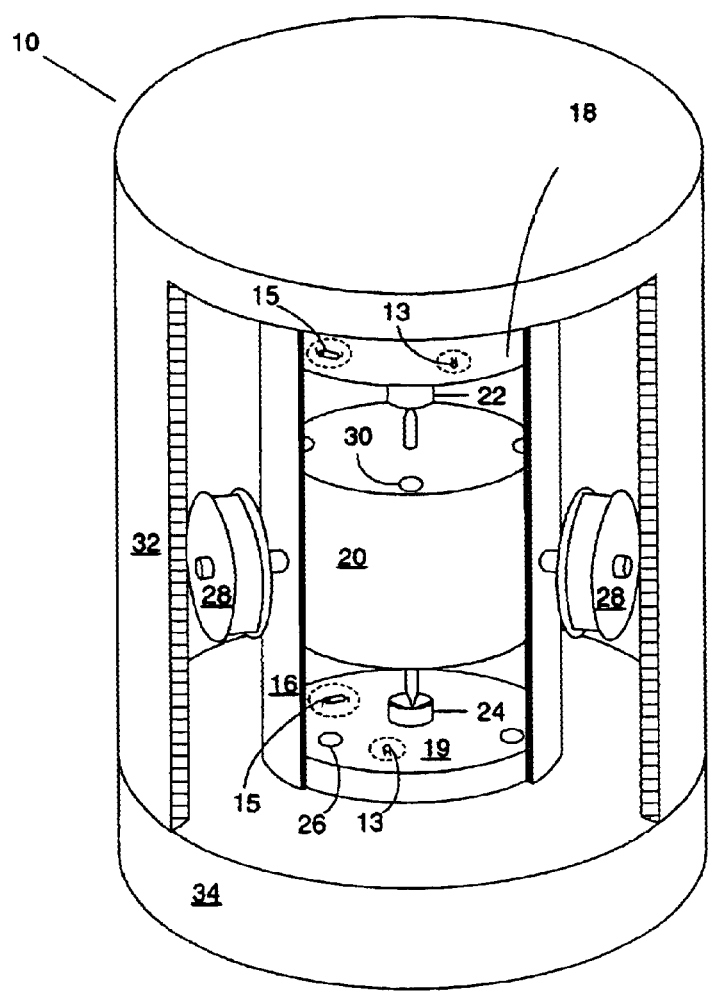
FIG. 1 is a perspective view of the mechanical arrangement of the components of the viscometer.

FIG. 1 shows a perspective view of the viscometer head 10 of the preferred embodiment of the free rotor viscometer. The viscometer housing, made up of upper housing 32 and lower housing 34 contains the mechanical portions of the viscometer. Inner wall 16 is a cylindrical sleeve that in combination with top wall 18 and bottom wall 19 form test chamber 17 for containing the fluid. Top wall 18 is cylinder shaped and extends down from upper housing 32. Bottom wall 19 is cylindrical and extends up from lower housing 34. Inner wall 16 is made of a non-magnetic material, such as aluminum or plastic. Ring gaskets (not shown) set in grooves around top wall 18 and bottom wall 19 form a fluid tight seal with inner wall 16 to contain the test fluid in test chamber 17.

Figure 2A:
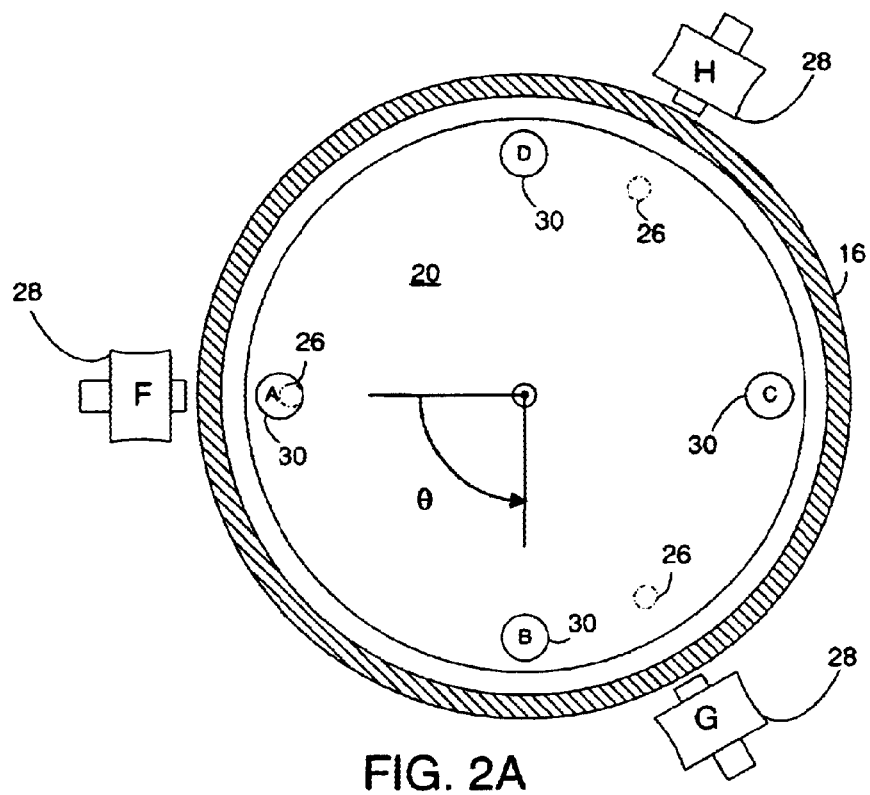
FIG. 2 shows the relationship of the rotor, rotor poles and electromagnets.

Cylinder shaped rotor 20 is disposed in test chamber 17, with its axis of rotation concentric with inner wall 16 as shown in FIG. 2A. Rotor 20 is held in place and rotates on jeweled bearings 22 and 24 mounted on top wall 18 and bottom wall 19. Stainless steel pivots mounted on the rotor top and bottom on the rotor's axis of rotation engage the jeweled bearings. Low friction bearings are important in the current invention as friction causes viscosity measurement errors.

Four ferrous inserts are located at 90-degree intervals around the axis of rotation of rotor 20 forming four magnetic poles 30 as shown in FIG. 2A. The ferrous inserts are 0.25 inch diameter rods aligned parallel to the rotor axis and extend substantially the full length of the rotor. Rotor 20 is made of a non-magnetic material. The space between the outer diameter of rotor 20 and inner wall 16 is uniform. In the preferred embodiment, the gap between the outer diameter of the rotor and the inner wall is 0.01 to 0.1 inches depending on the viscosity of the fluids to be measured. For ease of calculating the moment of inertia of rotor 20, it is desirable for the magnetic poles to have the same mass density as the rotor. A rotor with constant mass density can be formed by making the rotor out of non-magnetic stainless steel and the magnetic poles out of magnetic stainless steel.

Three electromagnets 28 are disposed around the test chamber. Electromagnets 28 are located at 120-degree intervals around a circle centered on rotor 20. The electromagnets are located at a height relative to rotor 20 such that the magnetic field of the electromagnet engages the rotor poles.

A coil of wire wound on a bobbin forms each electromagnet, the bobbin is disposed on a ferrous rod. The ferrous rods are aligned radially from the center of rotor 20. Electromagnet 28 coils in the preferred embodiment consist of 675 turns of 35 AWG wire. Typical current is 300 mA depending on fluid viscosity.

Each electromagnet 28 is energized by application of an electric current through the coil. When energized, an electromagnet produces a magnetic field and imposes a magnetic force on the closest rotor pole and pulls that rotor pole toward the electromagnet. Bearings 22 and 24 constrain rotor 20 to rotary movement, so the applied magnetic force results in an applied rotor torque, causing rotor 20 to rotate. The magnitude of the rotor torque is dependent on the magnetic field produced by the electromagnets and the geometry of the rotor and electromagnets. The geometry of the rotor and electromagnets is fixed and the rotor torque is proportional to the magnetic field produced by the electromagnets. The magnetic field is proportional to the electric current applied to the electromagnet. By precisely controlling the current applied to the electromagnets, rotor torque is precisely controlled.

The preferred embodiment has three electromagnets 28 and rotor 20 has four poles 30. Electromagnets 28 are energized in sequence to rotate rotor 20. One electromagnet is energized at a time. The electromagnet that is energized depends on rotor position.

FIG. 3 shows the commutation of electromagnets 28 versus rotor 20 position in tabular form. Column 1 lists rotor 20 position from zero degrees to 720 degrees, two complete revolutions of rotor 20. Rotor 20 position is given relative to the reference position shown in FIG. 2A. Column 2 lists the energized electromagnet for each position of rotor 20. Column 3 lists the pole of rotor 20 pulled toward the energized electromagnet for each position of rotor 20. FIG. 2A shows rotor 20 in the 0 degree position, pole B is thirty degrees away from electromagnet G. Energizing electromagnet G pulls pole B toward electromagnet G, rotating rotor 20 counterclockwise. Rotor 20 rotates toward electromagnet G until it reaches the 30 degree position where pole B is radially aligned with electromagnet G. Radial alignment is when a rotor pole is in line between an electromagnet and the center of rotor 20. Once the pole reaches radial alignment, the energized electromagnet cannot produce any further torque, so the next electromagnet in sequence is energized. The next electromagnet is energized until the next pole reaches radial alignment and the sequence continues to continuously rotate rotor 20. Twelve steps in the above sequence rotate rotor 20 through one complete revolution.

The sequence of energizing the electromagnets is called a commutation pattern. In the preferred embodiment, the commutation pattern consists of energizing the electromagnets in order in the direction of rotation. One complete rotation of the rotor requires twelve commutation steps, where each commutation step comprises de-energizing an electromagnet, energizing the next electromagnet in sequence for the time it takes to pull the rotor through 30 degrees of rotation until the rotor pole reaches radial alignment with the next electromagnet. In one complete rotor rotation each of the three electromagnets will be energized four times and each rotor pole will be pulled toward an electromagnet three times.

When a magnetic field of the same polarity is repeatedly imposed on a magnetic object, such as the rotor's magnetic poles, the object can gradually become magnetized. The attractive force of the magnetic object in the magnetic field is affected by this magnetization. Although this is a secondary factor, the applied rotor torque is affected by this magnetization and would vary over time. Rotor pole magnetization is avoided in the preferred embodiment by reversing the polarity of the current applied to the electromagnets, reversing the magnetic field polarity, on alternate attractions of each rotor pole. The last column of FIG. 3 lists the polarity of the magnetic field imposed on rotor 20 poles versus rotor position. The magnetic field polarity alternates between impositions of the magnetic field on each individual rotor pole. The implementation of rotor demagnetization in the preferred embodiment is exemplary, many variations of alternating magnetic field are possible which fall under the broad outline of the present invention.

Upper housing 32 including top wall 18 are made of magnetic material, such as iron, to provide a low reluctance path for the magnetic field produced by the electromagnets.

Three proximity sensors 26 sense rotor pole position. Each of the three proximity sensors 26 is associated with one electromagnet 28. Each proximity sensor 26 senses the position of a pole of rotor 20 relative to the associated electromagnet 28. The proximity sensor associated with the energized electromagnet detects radial alignment of a rotor pole with the energized electromagnet. A signal generated by the proximity sensor triggers the transition to the next step in the commutation pattern.

Figure 4:
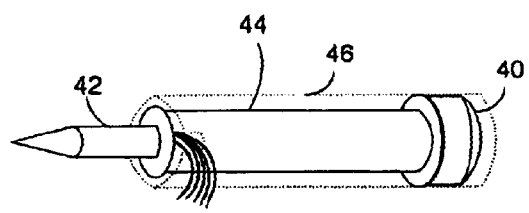
FIG. 4 is a detailed view showing the construction of a proximity sensor.

The proximity sensors in the preferred embodiment consist of a Hall sensor 40 biased by a magnetic field. FIG. 4 shows a diagram of proximity sensor 26. A coil of wire 44 wound on an iron nail 42 provides the bias field for the sensor. Shield 46 (drawn with dotted lines) around the bias coil and Hall sensor is made of a magnetic material, such as iron, and provides a path for the bias field. Each proximity sensor is recessed into bottom wall 19 underneath rotor 20 such that the top of the Hall sensor is flush with bottom wall 19. Each proximity sensor is positioned in approximate radial alignment with the associated electromagnet and is positioned so the rotor pole passes over top of the sensor. In operation, as a rotor pole passes over the sensor, the magnetic field path of the bias coil changes and the Hall sensor detects the change in the magnetic field and produces an electrical output signal. An amplifier and threshold amplifier driven by the Hall sensor electrical signal produce a trigger signal to the controller which affects electromagnet commutation.

In the preferred embodiment, coil 44 is driven with a constant current to produce the bias magnetic field. Coil 44 consists of 300 turns of 38 AWG wire wound on a 0.070 inch diameter iron nail and is driven by a constant current of 100 mA. The bias field could also be produced by a permanent magnet.

Many different proximity sensors and sensor configurations may be used to detect rotor position and trigger the electromagnet commutation timing and still fall within the broad outline of the present invention.

Lower housing 34 including bottom wall 19 are made of non-magnetic material to allow proximity sensors 26 to operate properly.

Figure 2B:
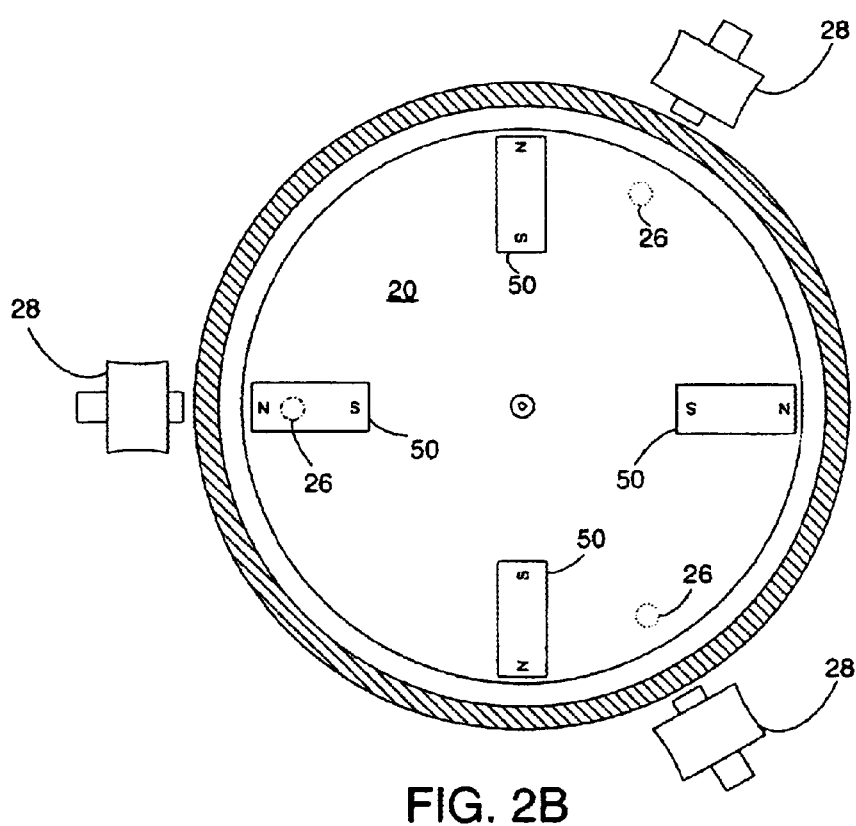

Rotor poles 30 can be formed from permanent magnets embedded in rotor 20. FIG. 2B shows a rotor configured with permanent magnet poles 50. Increased torque results from the combination of the electromagnet acting on permanent magnet poles. In this configuration, applied torque is a function of electromagnet field strength and permanent magnet field strength. Permanent magnets with stable magnetic field strength are important to maintain a known relationship between applied current and applied torque.

Viscosity is the ratio of shear stress to strain rate. Shear stress is inversely proportional to the space between the rotor and the test chamber inner wall. Strain rate is proportional to rotor rotation rate. Most of the parameters in the viscosity equation are physical constants in the viscometer design. The result is that viscosity is proportional to applied torque divided by rotation rate. Viscosity may be determined by applying a given torque and measuring the resulting rotation rate or measuring the torque required to achieve a given rotation rate.

The present invention produces very accurate and repeatable viscosity measurements by producing a constant torque and measuring rotor rotation rate. In practice, electromagnet drive current is selected to produce a torque that results in a rotation rate in a nominal range. The resulting rotation rate is precisely measured over multiple rotations. Viscosity is calculated from the ratio of the applied torque to rotation rate.

With fluid disposed in test chamber 17, the viscosity is determined by the equation:

$$\mu = \frac{T_s}{2\pi R_1^3 \omega} * \left[ \left( \frac{R_2 - R_1}{H} \right) + \left( \frac{2S}{R_1} \right) \right]$$

$\omega$ is the rotation rate in radians per second
$\mu$ is viscosity
$R_1$ is the radius of the rotor in meters
$R_2$ is the radius of the inner wall in meters
H is rotor height
$T_s$ is the applied torque
S is the distance between the rotor top or bottom and the test chamber The viscosity equation is similar to Newton's viscosity equation for concentric cylinders, additionally accounting for viscous drag on the rotor top and bottom. In practice, the magnitude of the viscous drag of rotor top and bottom needs to be accounted for to achieve the desired measurement accuracy.

In Newtonian fluids, viscosity is independent of strain rate. Thus, viscosity is constant over the normal range of strain rates. Measurement of either torque or rotation rate will produce the correct viscosity value. The preferred method of applying a constant torque and measuring rotation rate produces very accurate viscosity measurements.

In non-Newtonian fluids, viscosity is a non-linear function of strain rate. It is necessary to know the shear rate at which the viscosity measurement was taken. As a result, for non Newtonian fluids it is necessary to establish a given rotation rate, and its associated shear rate, and to measure the applied torque required to maintain that rotation rate in order to determine viscosity.

Fluid viscosity varies with fluid temperature. During viscosity measurements, fluid temperature must be known in order to accurately understand the viscosity measurement. The preferred embodiment contains two temperature sensors (not shown). One temperature sensor is located in top wall 18 and the other is located in bottom wall 19. Fluid temperature is assumed to be the average temperature measured by the two temperature sensors. In practice, if the temperatures read by the two sensors differ by more than a few degrees, the viscosity measurement should be performed after the fluid temperature stabilizes.

To understand the temperature dependence of viscosity in a test fluid, viscosity measurements are performed at multiple temperatures. The preferred embodiment contains heaters to warm the test fluid and test chamber. Test fluids exhibiting linear viscosity versus temperature may be characterized by viscosity measurements at two temperatures. Standard temperatures for characterizing fluid viscosity are 40 C. and 100 C.

Figure 5:
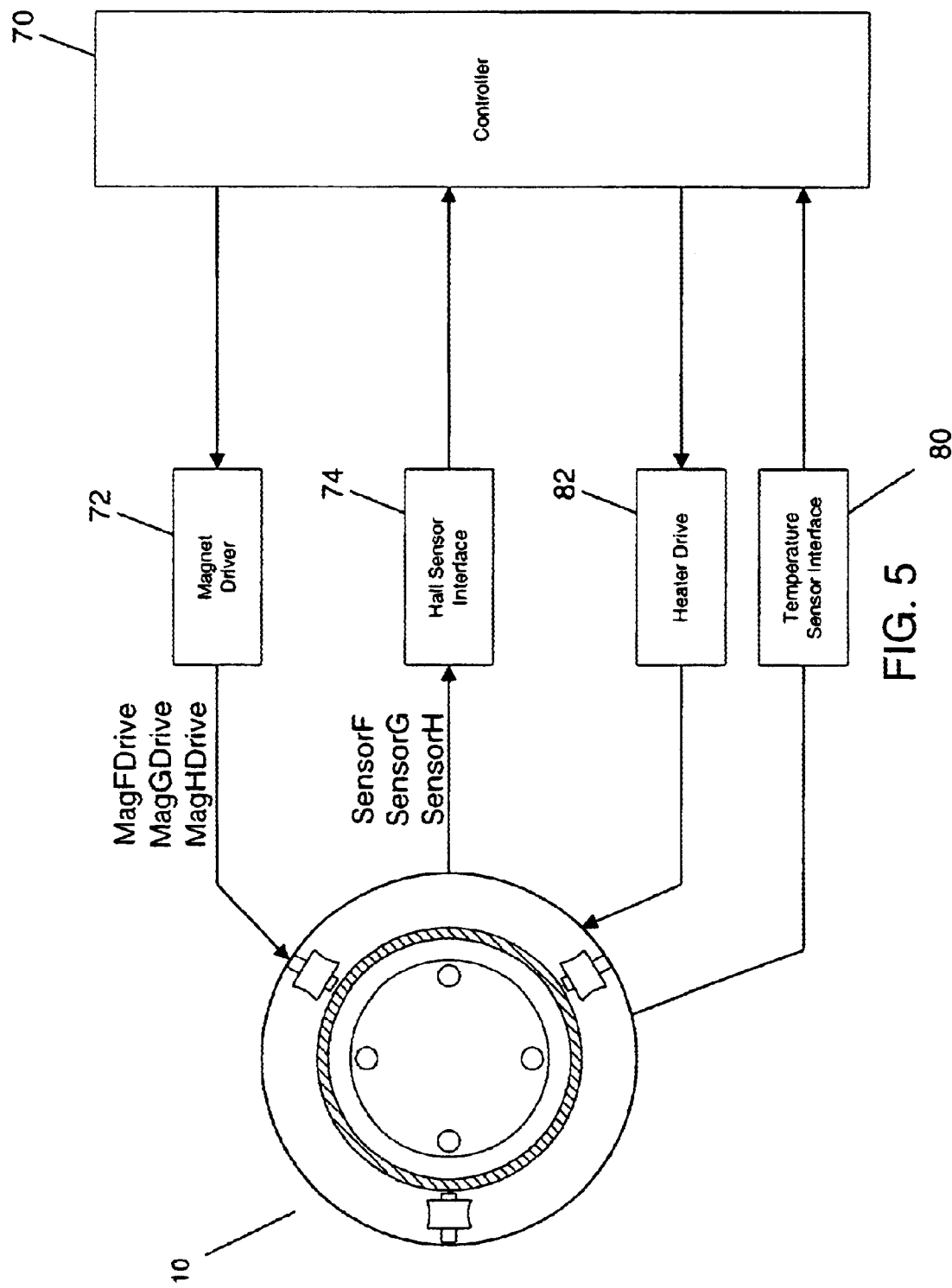
FIG. 5 is a schematic view of the viscometer.

FIG. 5 shows a schematic view of the viscometer connected to the control circuitry. Controller 70 consists of a microprocessor and associated memory and peripheral circuitry. The preferred embodiment uses a Microchip 17C44 microprocessor. Controller 70 energizes electromagnets 28 through magnet driver 72. The signals from the proximity sensors 26 are processed through Hall sensor interface 74 to produce a trigger signal. The trigger signal indicates that the rotor pole is radially aligned with the energized electromagnet and that the next electromagnet in sequence should be energized. Temperature sensors (not shown) drive the temperature sensor interface circuit 80, which allows controller 70 to read each of the temperature sensors. Heater drive 82 allows the controller to warm the test fluid and test chamber. Controller 70 uses temperature inputs to adjust the amount of heat applied to the viscometer to maintain a specific temperature setting.

Figure 8:
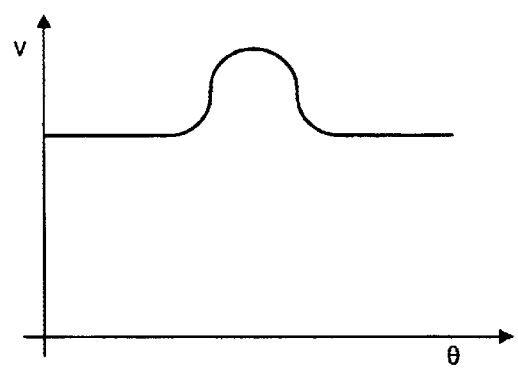
FIG. 8 shows the waveforms produced by the rotor position Hall sensors.

FIG. 8 shows a proximity sensor output signal as a rotor pole passes over the proximity sensor. The peak signal occurs when the rotor pole is directly above the proximity sensor.

Figure 6:
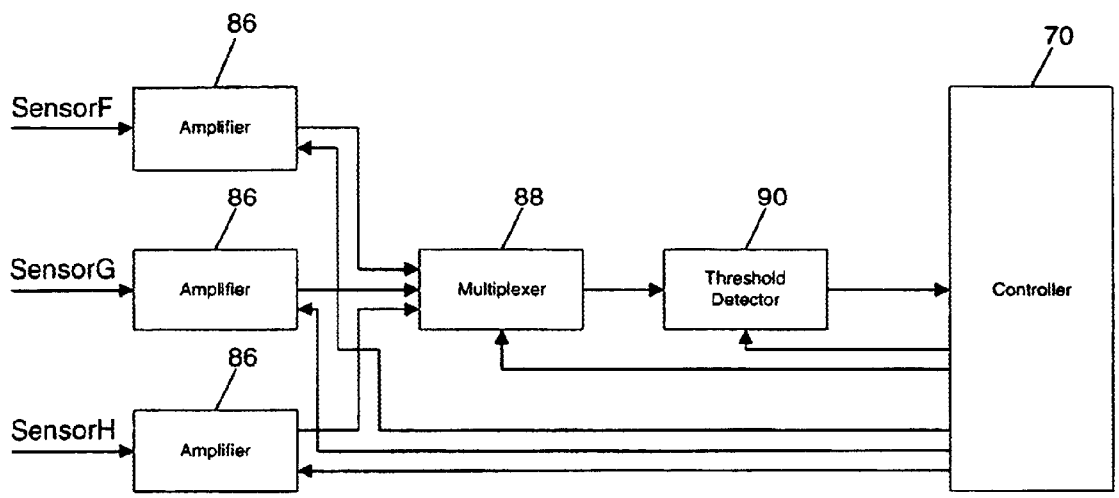
FIG. 6 is a block diagram of the sensor circuitry.

FIG. 6 is a block diagram detailing the workings of Hall sensor interface 74. The Hall sensor in each proximity sensor drives an amplifier 86. Controller 70 adjusts the gain of each amplifier individually to account for variation in Hall sensors. Controller 70 selects the active sensor through multiplexer 88. The active sensor is the proximity sensor associated with the energized electromagnet. Multiplexer 88 drives threshold detector 90. Controller 70 adjusts the trigger threshold level of threshold detector 90. The output of threshold 90 is a trigger signal used by controller 70 to trigger the transition to the next electromagnet commutation step. The preferred embodiment uses digitally controlled resistors to adjust the gains of amplifiers 86 and the threshold of threshold detector 90, however, many different ways exist to implement these functions including fixing the gain and threshold settings in hardware.

Figure 7:
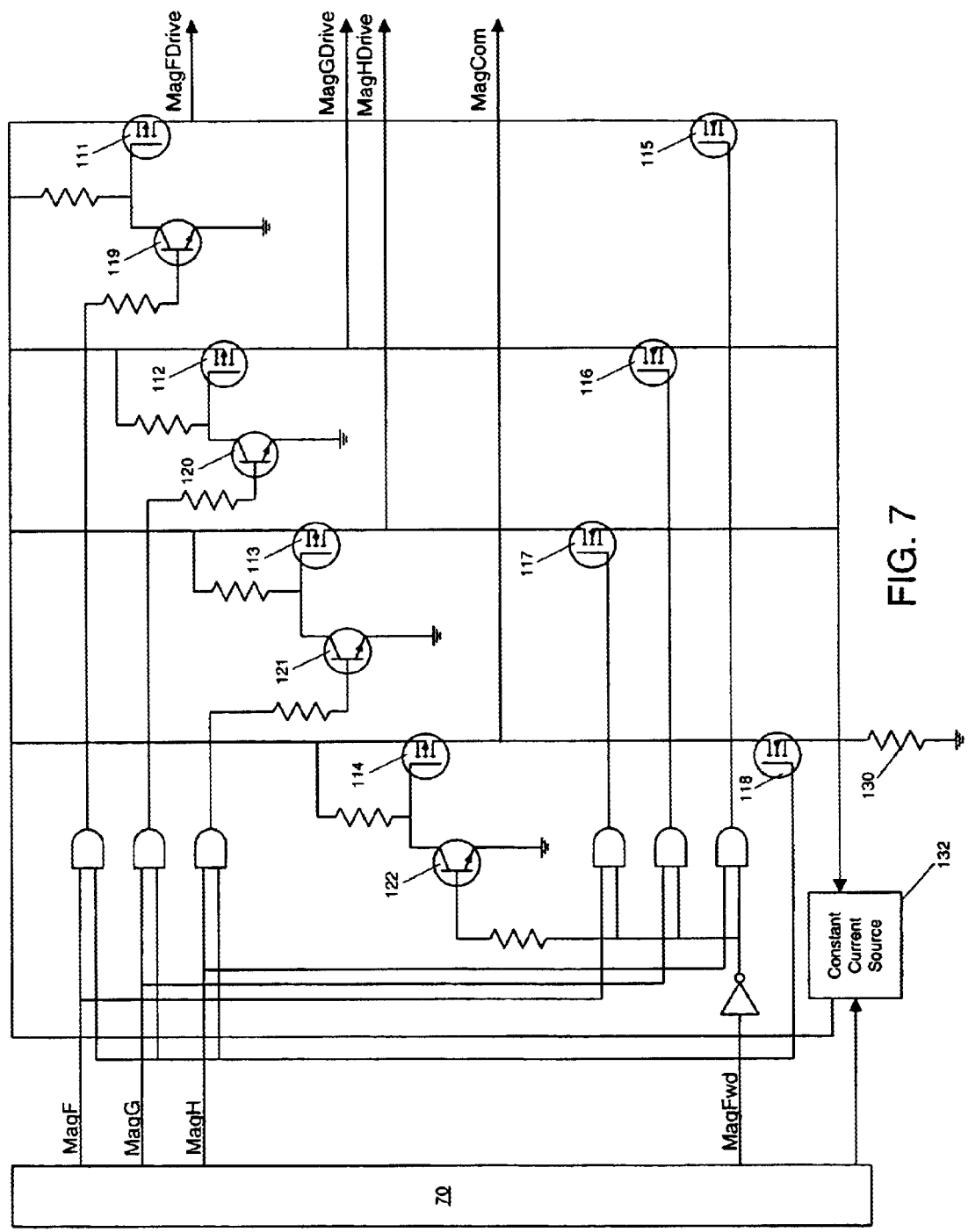
FIG. 7 is a detailed schematic of the electromagnet drive.

FIG. 7 details the electromagnet drive circuitry. One side of each electromagnet coil is tied to MagCom. The other ends of the electromagnet coils are connected respectively to MagFDrive, MagGDrive and MagHDrive. Transistors 111–118 form a conventional H-bridge circuit for each electromagnet such that the electromagnet may be energized with either North or South polarity from a single supply. Controller 70 via the MagFwd signal controls the polarity of the electromagnet drive. Controller 70 also controls which electromagnet is energized through signals MagF, MagG, and MagH. Transistor 119–122 provide translation of the control signals to drive high-side transistors 111–114, respectively.

Controller 70 selects an electromagnet coil current via a digitally controlled potentiometer in constant current source 132. Constant current source 132 senses electromagnet coil current by measuring the voltage across resistor 130 through which the electromagnet current flows and adjusts the voltage applied to the active electromagnet via transistors 111–114 to deliver a constant current which in turn provides a constant magnetic field.

Figure 9:
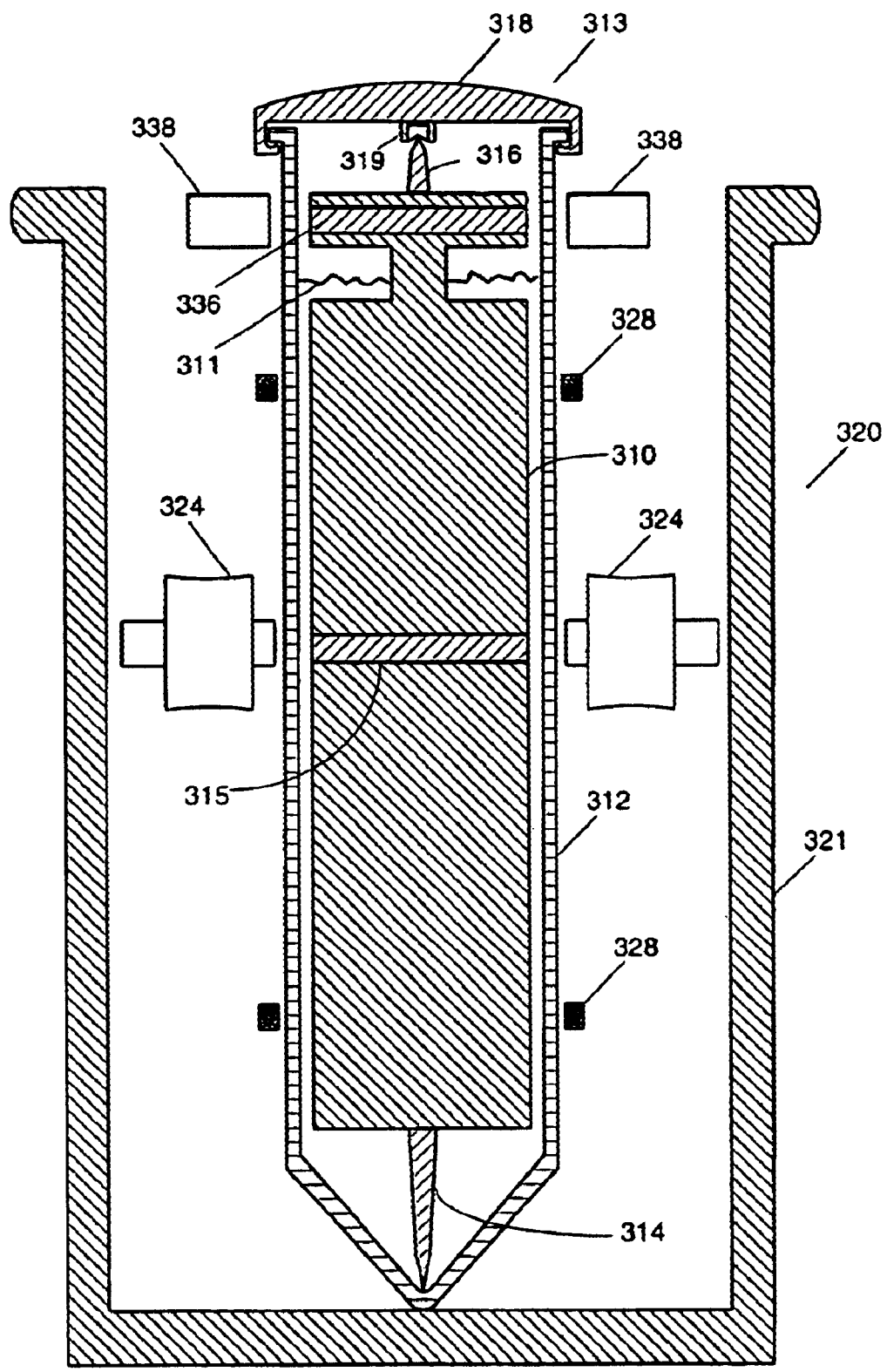
FIG. 9 is a cut away front view of alternative embodiment of the invention.

FIG. 9 shows an alternate embodiment of the invention. Test tube 312 and cap 318 form a sealed test chamber 313 for viscosity measurements. A generally cylindrical rotor 310 is disposed in test chamber 313. Rotor 310 is supported on the bottom by stainless steel pivot 314 mounted on the bottom of rotor 310 and concentric with rotor 310. Pivot 314 has a conical end that engages the conical bottom of test tube 312. Pivot 316 is similarly mounted on the top of rotor 310 and engages a spring loaded jeweled bearing 319 mounted on cap 318. The pivots and bearings position rotor 310 concentrically within the test tube and allow rotor 310 to rotate with very little friction. Ferrous insert 315 in rotor 310 forms two rotor poles across the diameter of rotor 310.

Figure 10:
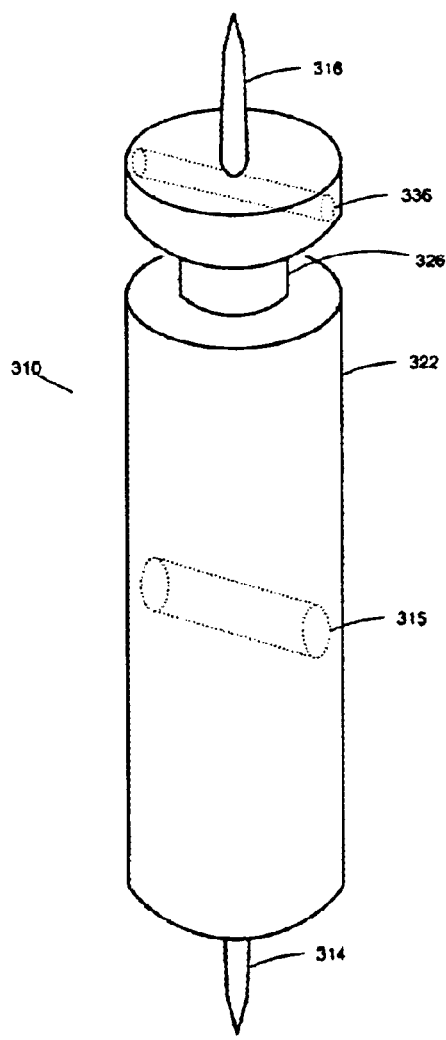
FIG. 10 is a perspective view of the rotor in the alternate embodiment.

FIG. 10 is a perspective view of rotor 310. Aluminum cylinder 322 applies shear stress to the test fluid between the outer diameter of cylinder 322 and the wall of test tube 312. Neck 326 reduces the criticality of fluid level to measurement accuracy. A test fluid fills the test chamber around the rotor cylinder 322, test fluid level 311 is above cylinder 322 in rotor neck 326.

To perform viscosity measurements, test chamber 313 is placed in viscosity test fixture 320. Test fixture 320 consists of a ferrous sleeve 321, a means to position and hold test chamber 313, electromagnets 324, and Hall rotor position sensors 338. Test chamber positioning means consists of two test chamber positioning rings 328, into which the test tube is inserted. The bottom of the test tube rests on the bottom of the ferrous sleeve and is constrained laterally by positioning rings 328. Positioning rings 328 are attached to and are in fixed positions relative to ferrous sleeve 321.

Figure 11:
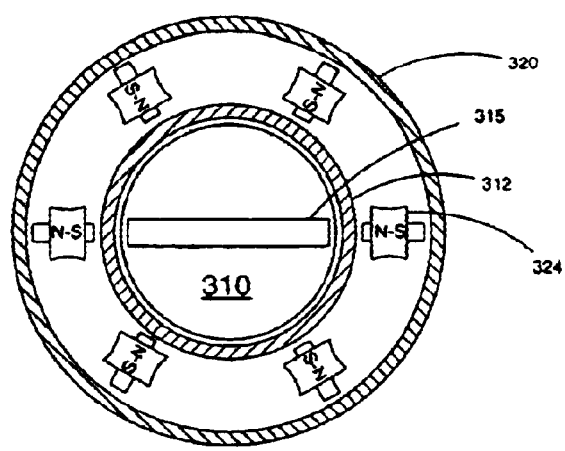
FIG. 11 is a top section view showing the electromagnets.

Electromagnets 324 in fixture 320 impose a magnetic force on ferrous insert 315 in rotor 310 within test chamber 313 and cause rotor 310 to rotate within the test fluid. FIG. 11 shows a cutaway top view of test fixture 320, test chamber 313, electromagnets 324, test tube 312, rotor 310 and ferrous insert 315. In this embodiment, a pair of electromagnets on opposite sides of the rotor is energized together. The energized pair of electromagnets pulls rotor poles 315 toward alignment with the electromagnets, causing the rotor to rotate. When the rotor position moves to the position where the ferrous insert is aligned with the pair of energized electromagnets, those two electromagnets are de-energized and the next pair of electromagnets, in the direction of rotation are energized, causing the rotor to continue rotating in that direction. With six electromagnets as shown, each step is 60 degrees, making six steps in one complete revolution of rotor 310. By employing 2N electromagnets where N is an odd number, and alternating the polarity of the electromagnets around the test chamber as shown, the ferrous rod is subject to alternating polarity from each successive electromagnet pair and consequently will not become magnetized. This arrangement simplifies the electromagnet drive required, because each electromagnet is energized with the same polarity each time.

Figure 12:
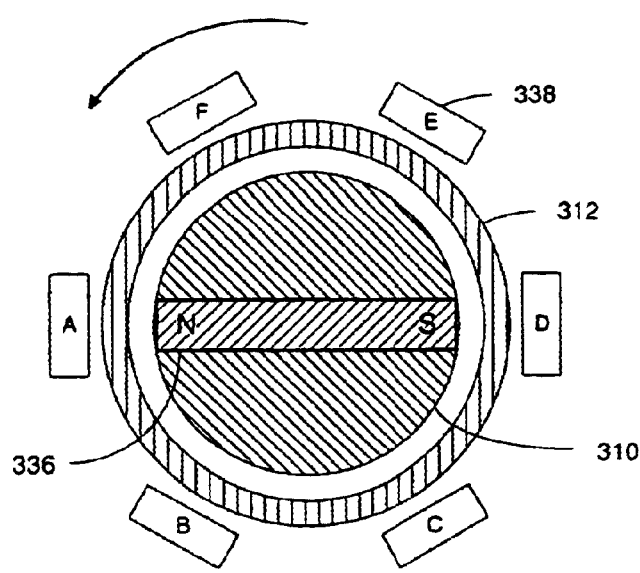
FIG. 12 is a top section view showing the Hall proximity sensors.
Figure 13A:
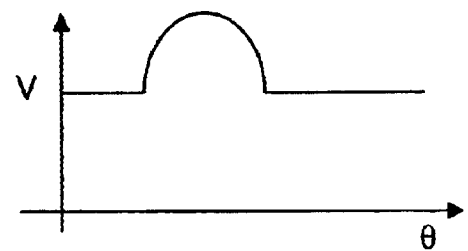
FIG. 13 shows proximity sensor waveforms.
Figure 13B:
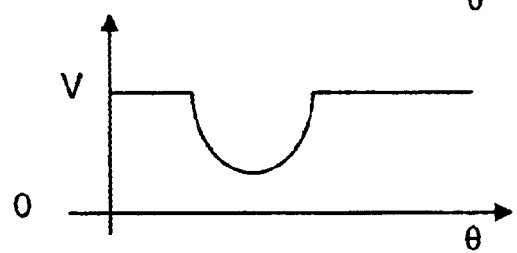
Figure 13C:
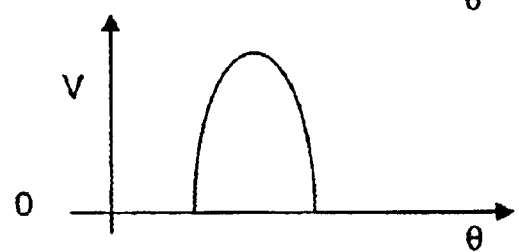
Figure 13D:
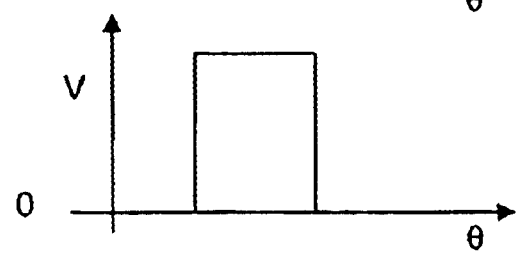

FIG. 12 shows a cut away top view of test fixture 320 and test chamber 313 specifically showing the arrangement of the rotor position sense magnet 336 and Hall proximity sensors 338 with respect to the test tube 312. Rotor position sense magnet 336 is a permanent magnet with North and South magnetic poles at opposite sides of rotor 310 diameter. FIG. 13A shows the output voltage from Hall sensor A as rotor 310 rotates counterclockwise past the A-D Hall sensor pair with the North pole of sense magnet 336 passing sensor A. Hall sensor outputs are offset above zero volts in their undetected state. Likewise FIG. 13B shows Hall sensor D output as the South pole of sense magnet 336 passes. FIG. 13C shows the voltage difference between Hall sensors A and D. FIG. 13D shows the trigger signal generated. A controller uses the trigger signal signal to commutate pairs of electromagnets to continuously rotate rotor 310.

It is understood that the details of these embodiments are exemplary and that other materials and arrangement of components may be implemented and still remain within the broad outline of the present invention.

What is claimed is:

1. An apparatus for measuring the viscosity of a fluid, said apparatus comprising:
    a) a test chamber for containing the fluid;
    b) a rotor disposed in the fluid in said test chamber, said rotor rotatably supported by a low friction support means on an axis of rotation;
    c) said rotor having a plurality of magnetic poles disposed about said axis;
    d) magnet means for producing a magnetic field and imposing a magnetic force on said magnetic poles, said magnetic force producing a rotor torque and rotating said rotor in the fluid at a rotation rate;
    e) a magnetic member, said magnetic member in magnetic contact with said magnet means and said magnetic poles, whereby a low reluctance path is formed through said magnet means, said magnetic poles, and said magnetic member;
    f) control means for controlling one of rotor torque and rotation rate; and
    g) sensing means for sensing one of rotor torque and rotation rate and producing a signal corresponding to the viscosity of the fluid.

2. The apparatus of claim 1 wherein said sensing means comprises at least one position sensor for sensing at least one position of said rotor and produces a position signal whose frequency corresponds to the rotation rate of the rotor and the viscosity of the fluid.

3. The apparatus of claim 1 wherein said magnet means further comprises power supply means for supplying current to produce the rotor torque and wherein said sensing means comprises means for measuring the current and producing a signal corresponding to the current required to rotate the rotor through the fluid and also corresponding to the viscosity of the fluid, whereby rotor torque is measured by measuring said current.

4. The apparatus of claim 1 wherein said test chamber is comprised of a cylindrical wall and a top and bottom wall, said top and bottom wall each having an inside surface, and wherein the low friction support means consists of bearings mounted on the inside surface of said top and bottom walls of said test chamber.

5. The apparatus of claim 1 wherein said magnet means comprises a plurality of separately operable electromagnets arranged in a generally circular pattern around said test chamber.

6. The apparatus of claim 5 further comprising:
    a) said sensing means for sensing angular rotor position and producing a rotor position signal; and
    b) said control means for sequentially activating said electromagnets, one electromagnet at one time; and in which said control means uses said position signal to determine when to sequentially activate the next electromagnet.

7. The apparatus of claim 1 wherein said sensing means comprises a plurality of proximity sensors arranged in a generally circular pattern proximate to said rotor, each of said proximity sensors having a proximity sensing field associated therewith, said sensing fields responsive to said rotor pole within said proximity sensing fields.

8. The apparatus of claim 1 further comprising a temperature sensor for sensing the temperature of the fluid and generating a temperature signal.

9. The apparatus of claim 8 further comprising said control means responsive to the temperature signal for energizing fluid heating means to produce heat for heating the fluid to a predetermined temperature.

10. The apparatus of claim 9 wherein the fluid heating means comprises a resistive heating element in thermal contact with the fluid in said test chamber.

11. The apparatus of claim 1 wherein said test chamber is removable.

12. The apparatus of claim 11 wherein said removable chamber is sealed.

13. The apparatus of claim 11 wherein said magnetic means comprises a plurality of separately operable electromagnets arranged in a generally circular pattern around said removable test chamber.

14. The apparatus of claim 13 further comprising:
    a) said sensing means for sensing angular rotor position and producing a rotor position signal; and
    b) said control means for sequentially activating said electromagnets, one electromagnet at one time; and in which said control means uses said position signal to determine when to sequentially activate the next electromagnet.

15. A viscosity tester for fluid comprising: a centrally disposed chamber for containing the fluid, having a cylindrical side wall, a circular bottom wall, and a circular top wall, said top and bottom walls having perimeters at side wall junctions, said top wall comprised of a magnetic material;
    b) a generally cylindrical rotor disposed in the fluid within said test chamber, said rotor rotatably supported by bearings on an axis of rotation;
    c) said rotor comprising a plurality of magnetic poles disposed about said axis;
    d) a plurality of electromagnets mounted in positions spaced around and proximate to said chamber side wall;
    e) a housing surrounding said electromagnets, said housing in magnetic contact with said top wall, whereby a low reluctance flux path is formed through said electromagnets, said rotor poles, said top wall, and said housing;
    f) a plurality of proximity sensors embedded in chamber bottom wall, a unique proximity sensor being associated with each of said electromagnets, each proximity sensor producing a sensor signal when a rotor pole is radially aligned with said associated electromagnet;
    g) an electric current supply;
    h) a control system interconnected with said current supply, said electromagnets, and said proximity sensors for selectively energizing said electromagnets sequentially in response to said sensor signals for imposing magnetic forces on said rotor, producing a rotor torque, and rotating said rotor within the fluid at a rotation rate; and i) means for producing an output signal corresponding to the viscosity of the fluid based on rotor torque and rotation rate.

16. A viscosity tester for fluid comprising:

a) a removable test chamber comprising a tube with a closed-end bottom and a circular opening at a top end, said circular opening sealed by a cap disposed over said circular opening and engaging said tube, said cap having an inside surface, said removable test chamber containing the fluid and a rotor disposed in the fluid, said rotor rotatably supported on an axis of rotation on bearings mounted on said inside surface of said cap and to said closed-end bottom of said test chamber, said rotor comprising a plurality of magnetic poles disposed about said axis of rotation and a position sense magnet;

b) said removable test chamber supported vertically in a test fixture comprising a plurality of electromagnets mounted in positions spaced around and proximate to said removable test chamber, a plurality of proximity sensors mounted in positions spaced around and proximate to said removable test chamber, a unique proximity sensor being associated with each of said electromagnets, each proximity sensor sensitive to the proximity of said rotor position sensing magnet and producing a sensor signal when a rotor pole is radially aligned with said associated electromagnet;

c) a magnetic member, said magnetic member in magnetic contact with said electromagnets whereby a low reluctance flux path is formed through said electromagnets said magnetic poles, and said magnetic member;

d) an electric current supply;

e) a control system interconnected with said current supply, said electromagnets, and said proximity sensors for selectively energizing said electromagnets sequentially, in response to said sensor signals, for imposing magnetic forces on said rotor, producing a rotor torque, and rotating said rotor within the fluid at a rotation rate; and f) means for producing an output signal corresponding to the viscosity of the fluid based on rotor torque and rotation rate.

17. A method for measuring the viscosity of a test fluid comprising:

a) disposing a rotor, rotatably supported by low-friction bearings on an axis of rotation, in the fluid, said rotor comprising magnetic poles disposed about said axis of rotation;

b) producing and imposing a magnetic force on said rotor poles producing a rotor torque and rotating said rotor within the fluid at a rotation rate;

c) providing a low reluctance flux path for said magnetic force;

d) controlling one of rotor torque and rotation rate; and d) repetitively sensing one of rotation rate and rotor torque and producing a signal corresponding to the viscosity of the fluid.

18. The method of claim 17 wherein said repetitively sensing is a step that comprises sensing the angular position of said rotor as it rotates producing an output signal corresponding to the rotation rate of the rotor and the fluid viscosity.

19. The method of claim 17 wherein said repetitively sensing is a step that comprises sensing a magnitude of electrical current corresponding to rotor torque which is required to rotate said rotor at a given rotation rate and producing a signal corresponding to fluid viscosity.

20. The method of claim 17 further comprising heating the fluid to a predetermined temperature.

21. The method of claim 20 further comprising measuring fluid viscosity at two or more distinct temperatures.

* * * * *